(12) United States Patent
Lee

(10) Patent No.: US 10,730,066 B2
(45) Date of Patent: Aug. 4, 2020

(54) PORTABLE NEBULIZER WITH A DUST SHIELD

(71) Applicant: Wen-Ching Lee, Taichung (TW)

(72) Inventor: Wen-Ching Lee, Taichung (TW)

( * ) Notice: Subject to any disclaimer, the term of this patent is extended or adjusted under 35 U.S.C. 154(b) by 114 days.

(21) Appl. No.: 15/468,837

(22) Filed: Mar. 24, 2017

(65) Prior Publication Data

US 2017/0291186 A1    Oct. 12, 2017

(30) Foreign Application Priority Data

Apr. 8, 2016   (CN) .......................... 2016 1 0216563

(51) Int. Cl.
| | | |
|---|---|---|
| *B05B 15/16* | (2018.01) | |
| *B05B 17/04* | (2006.01) | |
| *A61M 15/00* | (2006.01) | |
| *B05B 17/06* | (2006.01) | |
| *A61M 11/00* | (2006.01) | |
| *B05B 11/00* | (2006.01) | |
| *B05B 17/00* | (2006.01) | |

(52) U.S. Cl.
CPC .............. *B05B 17/04* (2013.01); *A61M 11/00* (2013.01); *A61M 11/005* (2013.01); *A61M 15/0025* (2014.02); *A61M 15/0085* (2013.01); *B05B 11/0032* (2013.01); *B05B 15/16* (2018.02); *B05B 17/06* (2013.01); *A61M 2205/276* (2013.01); *A61M 2205/8206* (2013.01); *B05B 17/0646* (2013.01)

(58) Field of Classification Search
CPC .. B05B 15/16; B05B 17/06; A61M 2205/276; A61M 2205/27; A61M 15/0025; A61M 15/0023
USPC .................................. 222/402.12, 321.3, 514
See application file for complete search history.

(56) References Cited

U.S. PATENT DOCUMENTS

| | | | | |
|---|---|---|---|---|
| 1,286,810 | A * | 12/1918 | Sheppard ............... | B65D 85/20 206/443 |
| 5,255,823 | A * | 10/1993 | Tichy .................. | B05B 11/0005 222/153.14 |
| 6,315,252 | B1 * | 11/2001 | Schultz ............... | B60R 11/0252 108/44 |
| 2012/0285446 | A1 * | 11/2012 | Van Der Mark .... | A61M 11/005 128/200.14 |

\* cited by examiner

*Primary Examiner* — Jason J Boeckmann
(74) *Attorney, Agent, or Firm* — Muncy, Geissler, Olds & Lowe, P.C.

(57) ABSTRACT

A portable nebulizer includes a nebulizer body including a nozzle hole and an atomizer plate positioned in the nozzle hole, and a dust shield coupled to the nebulizer body and movable relative to the nebulizer body between a dust protection position where the dust shield shields the nozzle hole of the nebulizer body and an open position where the dust shield is kept away from the nozzle hole of the nebulizer body, thus, the dust shield is capable of protecting the nozzle hole of the portable nebulizer against environmental contamination.

1 Claim, 8 Drawing Sheets

PORTABLE NEBULIZER WITH A DUST SHIELD

BACKGROUND OF THE INVENTION

1. Field of the Invention

Figure 1:
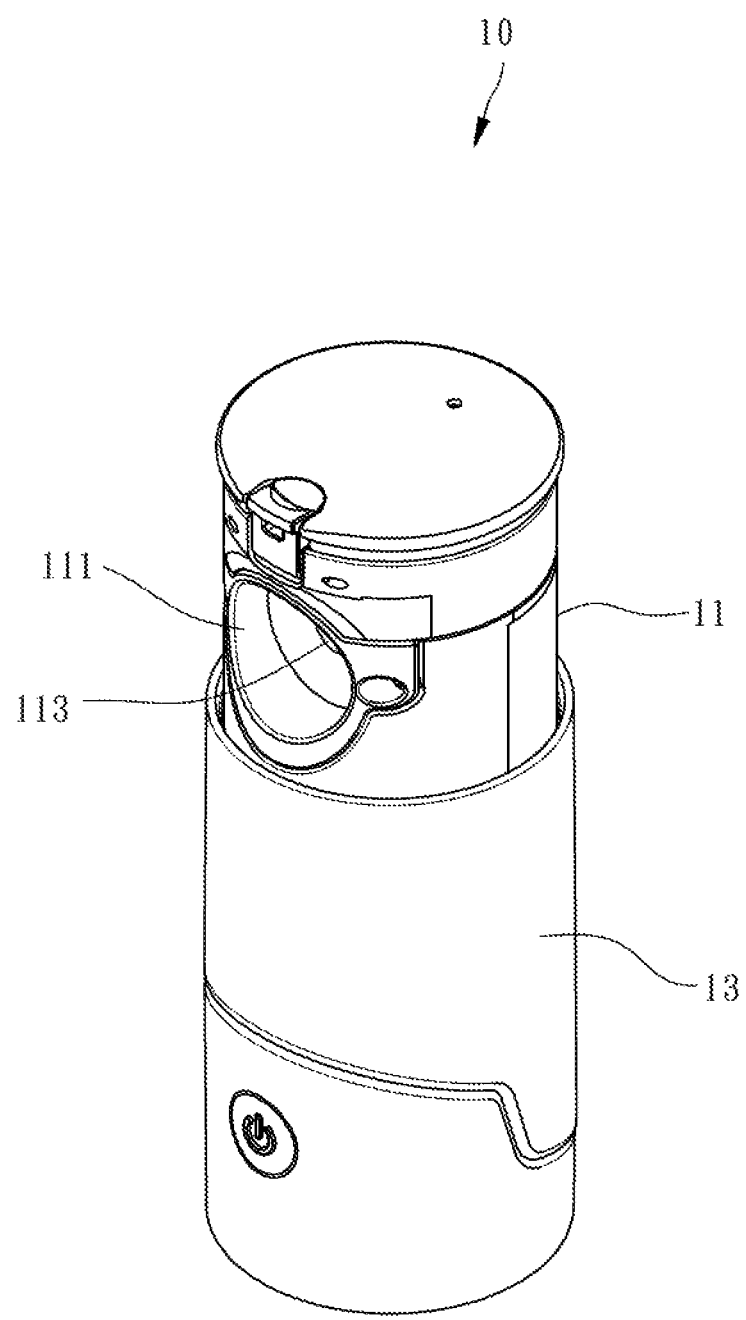
Figure 2:
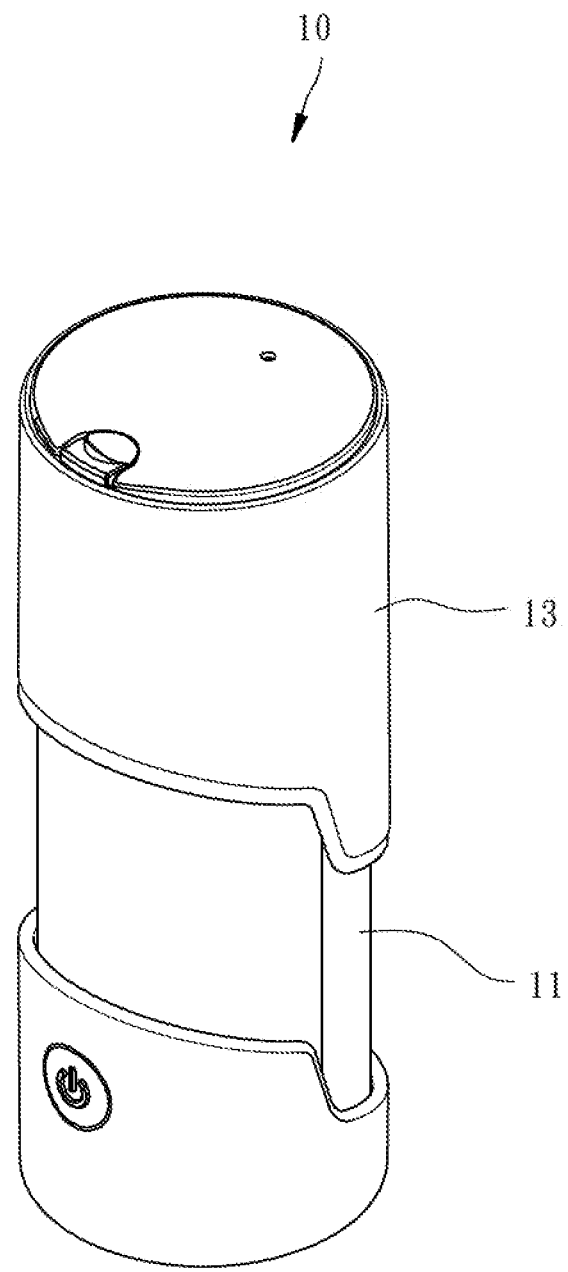
Figure 3:
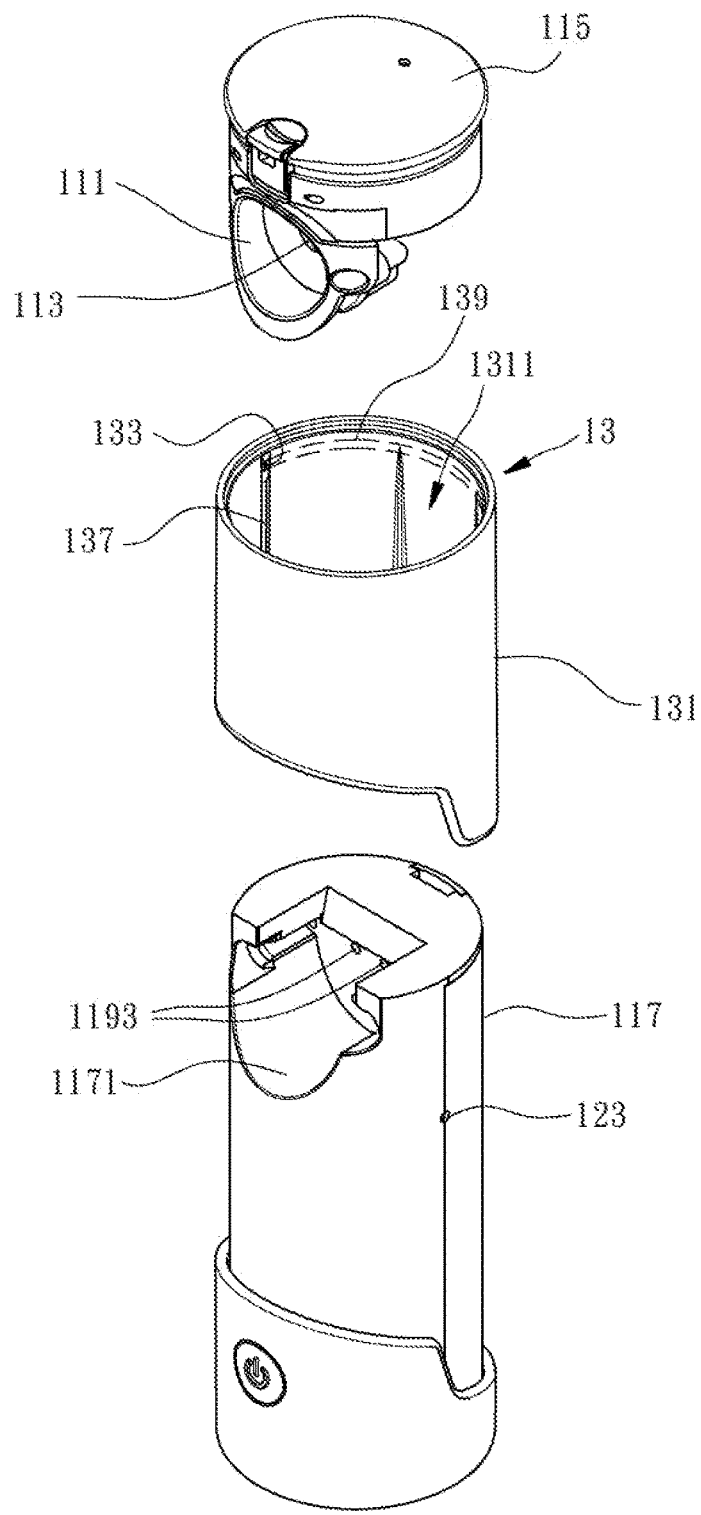
Figure 4:
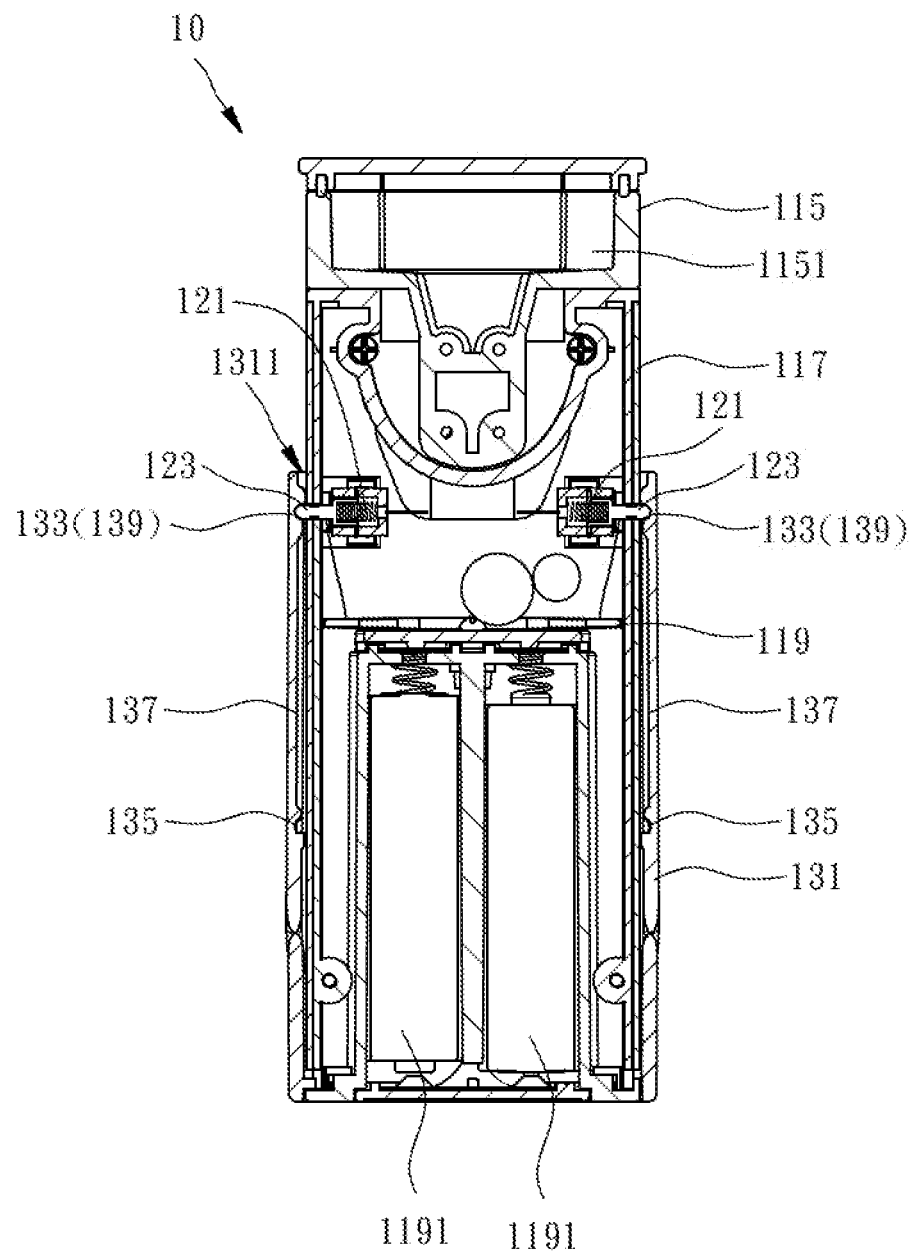
Figure 5:
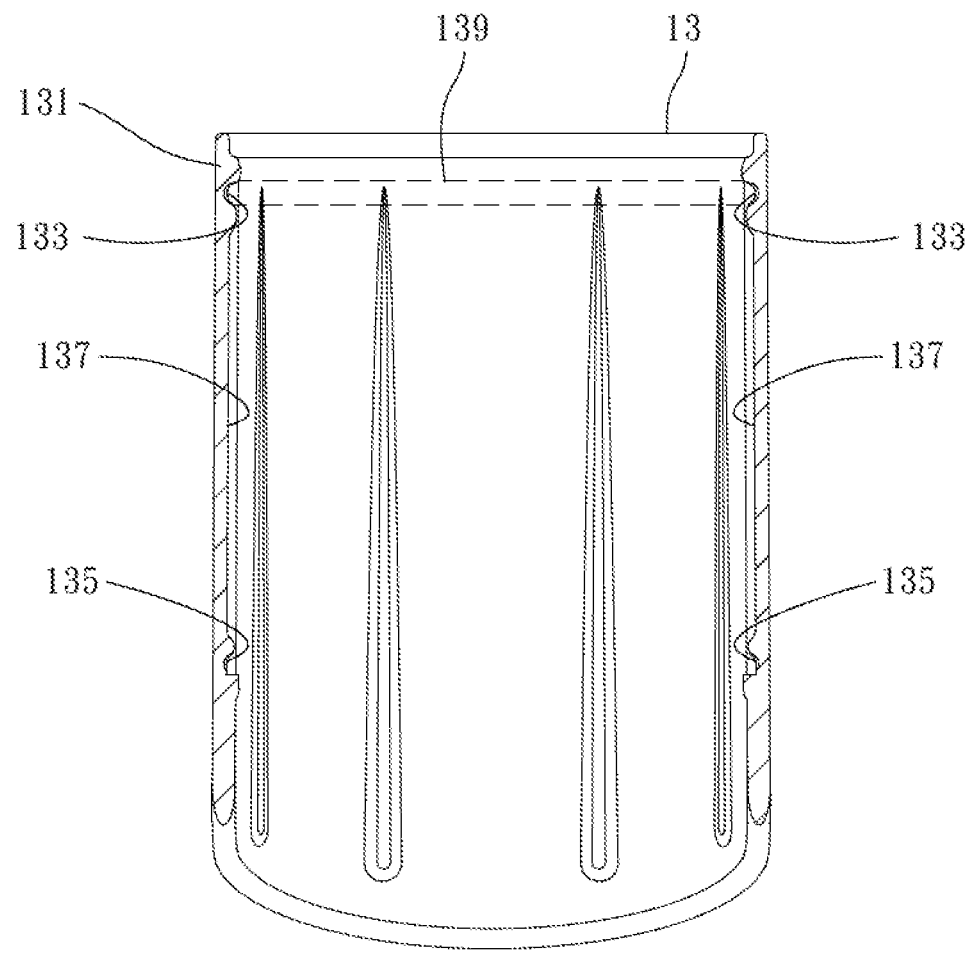
Figure 6:
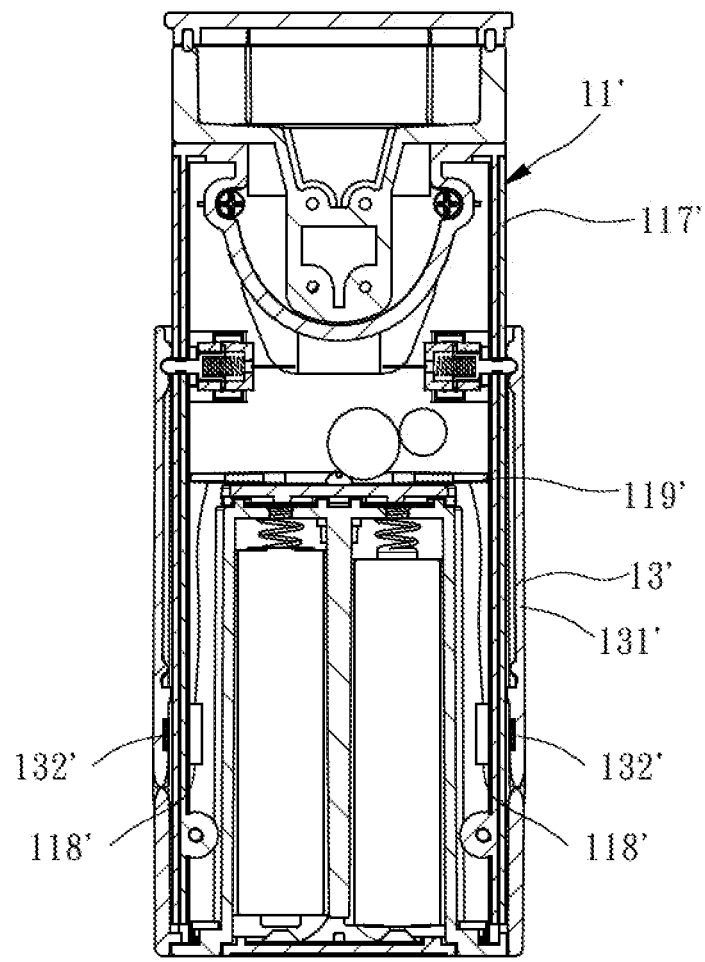

The present invention relates to nebulizer technology and more particularly, to a portable nebulizer that is equipped with a dust shield.

2. Description of the Related Art

A nebulizer is a device that turns liquid into a mist of fine droplets. It has a wide range of applications, for example, it can be used for real life application to increase the humidity and to make changes in environmental changes, or for medical application to turn medicine liquid into a mist.

Because a residual mist will be left around the nozzle hole of the nebulizer after each use of the nebulizer, causing dust to be adhered thereto, thus, after a long use, the nozzle hole and atomizer of the nebulizer tends to be covered with dust, affecting the atomization performance of the atomizer.

SUMMARY OF THE INVENTION

The present invention has been accomplished under the circumstances in view. It is therefore the main object of the present invention to provide a portable nebulizer, which is equipped with a dust shield that is capable of protecting the nozzle hole and atomizer plate of the nebulizer body of the portable nebulizer against environmental contamination.

To achieve this and other objects of the present invention, a portable nebulizer comprises a nebulizer body and a dust shield. The nebulizer body comprises a nozzle hole, and an atomizer plate positioned in the nozzle hole. The dust shield is coupled to the nebulizer body, and movable relative to the nebulizer body between a dust protection position where the dust shield shields the nozzle hole of the nebulizer body and an open position where the dust shield is kept away from the nozzle hole of the nebulizer body.

Thus, the dust shield is capable of protecting the nozzle hole of the portable nebulizer against environmental contamination.

Other advantages and features of the present invention will be fully understood by reference to the following specification in conjunction with the accompanying drawings, in which like reference signs denote like components of structure.

BRIEF DESCRIPTION OF THE DRAWINGS

FIG. 1 is an elevational view of a portable nebulizer with a dust shield thereof in an open position in accordance with a first embodiment of the present invention.

FIG. 2 corresponds to FIG. 1, illustrating the dust shield in a dust protection position.

FIG. 3 is an exploded view of the portable nebulizer in accordance with the first embodiment of the present invention.

FIG. 4 is a sectional view of the portable nebulizer in accordance with the first embodiment of the present invention.

FIG. 5 is a sectional view of the dust shield of the portable nebulizer in accordance with the first embodiment of the present invention.

FIG. 6 is a sectional view of the first embodiment of the present invention, illustrating the structure of the alternate form of the dust shield of the portable nebulizer.

FIG. 7 is a schematic drawing illustrating a dust shield of a portable nebulizer in an open position in accordance with a second embodiment of the present invention.

FIG. 8 corresponds to FIG. 7, illustrating the dust shield in a dust protection position.

DETAILED DESCRIPTION OF THE INVENTION

The composition, effects and features of the present invention will be more fully understood by way of examples in conjunction with the accompanying drawings, in which the components, size and outer appearance of the portable nebulizer are simply for explanation of the technical features of the present invention but not intended for use as limitations.

Referring to FIGS. 1 and 2, a portable nebulizer 10 in accordance with a first embodiment of the present invention is shown. The portable nebulizer 10 comprises a nebulizer body 11 and a dust shield 13. The nebulizer body 11 comprises a nozzle hole 111, and an atomizer plate 113 disposed inside the nozzle hole 111. The dust shield 13 is coupled to the nebulizer body 11 and movable relative to the nebulizer body 11 between an open position (see FIG. 1) and a dust protection position (see FIG. 2).

When the dust shield 13 is located at the open position, the dust shield 13 is kept away from the nozzle hole 111 of the nebulizer body 11, enabling the mist that is transformed from a liquid by the atomizer plate 113 to be spayed out of the nozzle hole 111 of the nebulizer body 11. When the dust shield 13 is located at the dust protection position, the dust shield 13 shields the nozzle hole 111 of the nebulizer body 11, preventing adherence of surrounding cotton dust and dirt to the nozzle hole 111 and atomizer plate 113 of the portable nebulizer 10.

As illustrated in FIG. 3 and FIG. 4, the nebulizer body 11 further comprises a first body shell 115, a second body shell 117 and an electronic driver 119. The first body shell 115 defines therein a liquid chamber 1151 adapted for holding water, essential oil, liquid medicine, etc. The atomizer plate 113 is connected to the first body shell 115, and disposed inside the liquid chamber 1151. The nozzle hole 111 is located on the outer surface of the first body shell 115. The electronic driver 119 is fixedly connected to the second body shell 117 and disposed inside the second body shell 117. In this first embodiment, the electronic driver 119 comprises a driving circuit (not shown), and two battery cells 1191 for providing the driving circuit with the necessary working electricity. The driving circuit 119 can be selected from a circuit composition known in the art, and therefore, we do not repeat it here. The battery cells 1191 can be secondary battery cells, or replaceable battery cells. The first body shell 115 is detachably mounted on the second body shell 117. After mounted the first body shell 115 on the second body shell 117, the atomizer plate 113 in the first body shell 115 is electrically connected to the electronic driver 119 in the second body shell 117 so that the electronic driver 119 is controllable to drive the atomizer plate 113 in generating a mist.

As illustrated in FIG. 3, the second body shell 117 defines therein an accommodation chamber 1171 adapted for accommodating a lower half of the first body shell 115 to let the electrodes (not shown) of the atomizer plate 113 of the first body shell 115 be electrically connected to the respective electrodes 1193 of the electronic driver 119 in the accommodation chamber 1171 of the second body shell 117. The structure of the electrodes of the atomizer plate 113 of the first body shell 115 and the electrodes 1193 of the electronic driver 119 and the connection therebetween are well known in the art, and therefore, we do not repeat them.

The nebulizer body 11 further comprises two springs 121 and two protruding rods 123. The two springs 121 are respectively mounted inside the second body shell 117. The two protruding rods 123 are respectively connected to the springs 121 and protruded over the outer surface of the second body shell 117. When the protruding rods 123 are forced to retract by an external force, the springs 121 are compressed by the respective protruding rods 123. When the external force disappears, the springs 121 immediately push the respective protruding rods 123 out of the outer surface of the second body shell 117. In this first embodiment, the springs 121 and the protruding rods 123 can be configured and assembled to create pogo pins, however, the use of pogo pins is not a limitation.

The dust shield 13 in this embodiment is a sliding sleeve 131. The sliding sleeve 131 defines therein a hollow passage 1311, two open recesses 133 and two dust protection recesses 135. The two dust protection recesses 135 and the two open recesses 133 are respectively located on the sliding sleeve 131 and disposed in communication with the hollow passage 1311. The second body shell 117 is disposed inside the hollow passage 1311 of the sliding sleeve 131. When the two protruding rods 123 are respectively engaged into the two open recesses 133, the dust shield 13 is held in the open position. When the two protruding rods 123 are respectively engaged into the dust protection recesses 135, the dust shield 13 is held in the dust protection position.

In this first embodiment, when the two protruding rods 123 of the second body shell 117 are kept away from the two dust protection recesses 135 and the two open recesses 133, the dust shield 13 is freely rotatable. Further, the dust protection recesses 135 and the open recesses 133 are curved inwardly from the inner perimeter of the sliding sleeve 131 toward the outer perimeter of the sliding sleeve 131. Alternatively, the dust protection recesses 135 and the open recesses 133 can be configured to cut through the inner and outer perimeters of the sliding sleeve 131. Therefore, the dust protection recesses 135 and the open recesses 133 can be formed on the sliding sleeve 131 in any of various different configurations, further, the number of the dust protection recesses 135 and the open recesses 133 is not limited to 2.

The sliding sleeve 131 further comprises two guide grooves 137. These two guide grooves 137 are formed on the sliding sleeve 131 with the respective open sides thereof respectively disposed in communication with the hollow passage 1311 of the sliding sleeve 131. The dust protection recesses 135 and the open recesses 133 are respectively disposed at respective two opposite ends of the guide grooves 137, thus, the two protruding rods 123 can be respectively arranged in the guide grooves 137, and moved along the respective guide grooves 137 between the dust protection position and the open position.

In this first embodiment, the two guide grooves 137 of the sliding sleeve 131 are straight grooves, however in actual application, the straight design is not a limitation. For example, the guide grooves 137 can be configured to exhibit an arched or spiral profile. Because the configuration of the guide grooves 137 is not limited to the design shown in the annexed drawings, the open position and the dust protection position are not limited to the arrangement of locating on the two opposite ends of a straight line. Further, because the dust shield 13 is slidably or rotatably coupled to the second body shell 117, using the dust shield 13 at the second body shell 117 to achieve dust protection should be included within the scope of the spirit of the present invention. Accordingly, the invention is not to be limited to the description (illustration) of the present first embodiment.

As illustrated in FIG. 5, the dust shield 13 further comprises a conductor 139. The conductor 139 is connected to the sliding sleeve 131. The conductor 139 has two opposite ends thereof respectively positioned in the two open recesses 133. Further, the conductor 139 can be embedded in the sliding sleeve 131, or connected to the inside wall of the sliding sleeve 131. The two protruding rods 123 are electrically connected to the electronic driver 119 (see FIG. 4). When the dust shield 13 is located at the open position, the electronic driver 119 is activated. At this time, the two protruding rods 123 are respectively stopped against the two open recesses 133 to achieve electric conduction between the protruding rods 123 and the conductor 139, therefore, the electronic driver 119 is triggered, driving the atomizer plate 113 to generate a mist. In FIG. 4, the open recesses 133 and the conductor 139 are superimposed, the reference number 139 of the conductor is synchronously indicated in the drawing using a parentheses. When the dust shield 13 is located at dust protection position, the two protruding rods 123 are respectively stopped against the respective dust protection recesses 135. At this time, the two protruding rods 123 are electrically disconducted to turn off the electronic driver 119, and therefore, the electronic driver 119 is not activated, and the atomizer plate 113 does no work.

Referring to FIG. 6, an alternate form of the aforesaid dust shield 13 is shown. As illustrated, the dust shield of this alternate form, referenced by 13', comprises a sliding sleeve 131' and a magnet 132'. The magnet 132' is connected to the sliding sleeve 131'. Preferably, the magnet 132' is embedded in the sliding sleeve 131'. The nebulizer body 11' further comprises a magnetic sensing element 118'. The magnetic sensing element 118' is fixedly connected to the second body shell 117', and electrically connected to the electronic driver 119' for controlling on/off of the electronic driver 119'. In this embodiment, the magnetic sensing element 118' is, but not limited to, a Hall sensor. When the sliding sleeve 131' of the dust shield 13' is located at the open position, the magnetic sensing element 118' detected the major part of the magnetic force or the strongest magnetic force of the magnet 132', and thus, the magnetic sensing element 118' triggers the electronic driver 119', causing the atomizer plate to work. When the sliding sleeve 131' of the dust shield 13' is moved out of the open position or moved to the dust protection position, the magnetic sensing element 118' is unable to detect the magnetic force of the magnet 132', or simply able to detect a micro magnetic force, thus, the electronic driver 119' is not activated and, the atomizer plate does no work.

Although two methods for triggering the electronic driver 119 are described, however, any other measure can be selectively used to trigger the electronic driver 119 when the dust shield is located at the open position, and therefore, the above-described two electronic driver triggering methods are not intended for use to limit the scope of the present invention.

Further, in the aforesaid first embodiment of the present invention, the sliding sleeve of the dust shield has a hollow passage defined therein, however, in actual application, the sliding sleeve can be configured without the hollow passage, for example, in the form of a half round cover or any other structure capable of covering the nozzle hole, and therefore, the sliding sleeve is not limited to the embodiment described above.

Figure 7:
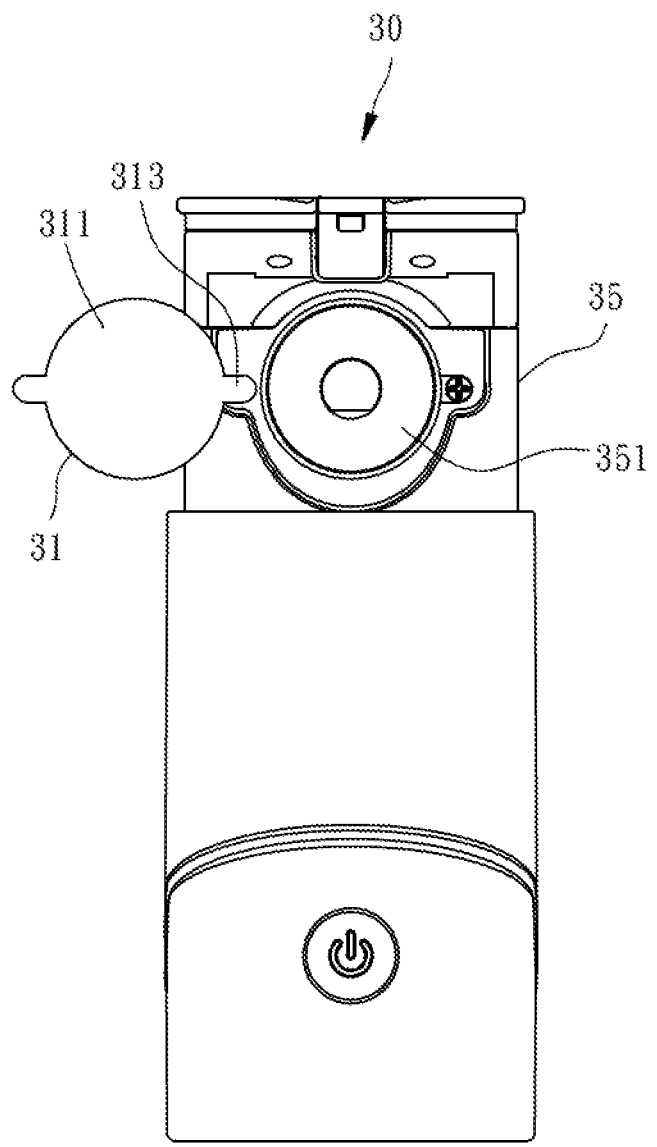
Figure 8:
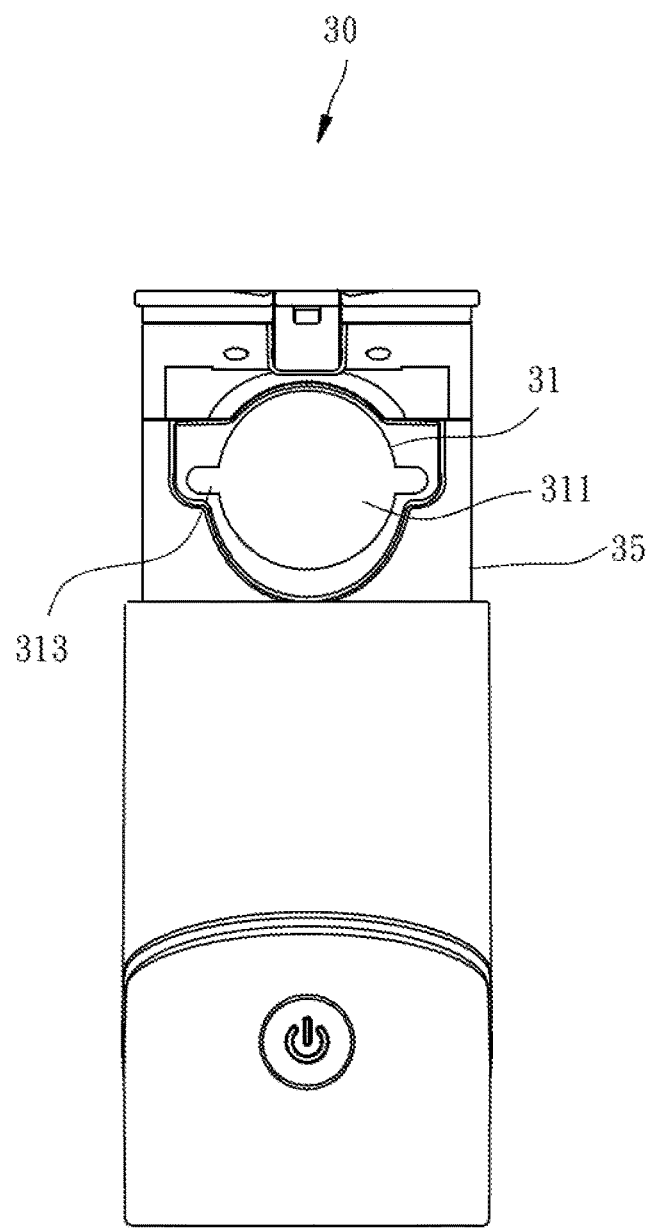

Referring to FIGS. 7 and 8, a portable nebulizer 30 in accordance with a second embodiment is shown. This second embodiment is substantially similar to the aforesaid first embodiment with the exceptions as described hereinafter. The dust shield 31 is not slidably sleeved onto the second body shell 33. In this second embodiment, the dust shield 31 comprises a dust protection sheet 311 and a connecting strip 313. The connecting strip 313 is extended from the border edge of the dust protection sheet 311 and pivotally connected to the first body shell 35 so that the dust shield 31 can be rotated or biased relative to the first body shell 35.

When the dust shield 31 is located at the dust protection position, the dust protection sheet 311 shields the nozzle hole 351 of the first body shell 35. Further, the dust protection sheet 311 of the dust shield 31 can be moved away from the dust protection position, enabling the dust shield 31 to be positioned in the open position. In this embodiment, the dust protection sheet 311 is biasable and rotatable with the connecting strip 313 relative to the first body shell 35. The dust shield 31 is preferably made from silicon rubber, rubber, or elastic plastics. Further, the shape of the dust shield is not limited to that described in the specification and illustrated in the drawings.

As described above, the dust shield and the nebulizer body can be connected together in any of various measures, avoid disconnection of the dust shield from the nebulizer body and lost. Further, in the aforesaid two embodiments, the nebulizer body consists of a first body shell and second body shell, however, in actual application, the nebulizer body can be a one piece member, and therefore, the structure of the nebulizer body is not limited to the aforesaid first and second embodiments.

Although particular embodiments of the invention have been described in detail for purposes of illustration, various modifications and enhancements may be made without departing from the spirit and scope of the invention. Accordingly, the invention is not to be limited except as by the appended claims.

What is claimed is:
1. A portable nebulizer, comprising:
a nebulizer body comprising a nozzle hole and an atomizer plate positioned in said nozzle hole; and
a dust shield coupled to said nebulizer body and movable relative to said nebulizer body along a surface of said nebulizer body between a dust protection position where said dust shield shields said nozzle hole of said nebulizer body and an open position where said dust shield is kept away from said nozzle hole of said nebulizer body;
wherein said nebulizer body further comprises a first body shell, a second body shell and an electronic driver, said first body shell defining therein a liquid chamber; said atomizer plate is connected to said first body shell and positioned in said liquid chamber; said nozzle hole is located on an outer surface of said first body shell; said electronic driver is connected to said second body shell and adapted for driving said shell atomizer plate when said first body shell is connected to said second body shell; said dust shield is connected to said second body shell and movable relative to said second body shell between said dust protection position and said open position;
wherein said electronic driver is enabled to drive said atomizer plate when said dust shield is located at said open position; said electronic driver is disabled when said dust shield is located at said dust protection position;
wherein said nebulizer body further comprises two protruding rods protruding over an outer surface of said second body shell and electrically coupled to said electronic driver; said dust shield comprises a sliding sleeve and a conductor, said sliding sleeve comprising an inner surface defining a hollow passage, two open valleys and two dust protection valleys, said two open valleys and said two dust protection valleys being disposed in communication with said hollow passage, said conductor being connected to said sliding sleeve and having two opposite ends thereof respectively positioned in said two open valleys, said two protruding rods being respectively located in the said two opposite ends of said conductor in the respective said open valleys to enable said electronic driver for triggering said atomizer plate when said dust shield is located at said open position, said two protruding rods being respectively located in said two dust protection valleys and said electronic driver is disabled when said dust shield is located at said dust protection position.

* * * * *